(12) United States Patent
Bal et al.

(10) Patent No.: US 8,306,185 B2
(45) Date of Patent: Nov. 6, 2012

(54) RADIOTHERAPEUTIC TREATMENT PLAN ADAPTATION

(75) Inventors: Matthieu Bal, Cadier en Keer (NL); Lothar Spies, Hamburg (DE); Todd R. McNutt, Severna Park, MD (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 848 days.

(21) Appl. No.: 11/573,564

(22) PCT Filed: Jul. 28, 2005

(86) PCT No.: PCT/IB2005/052554
§ 371 (c)(1),
(2), (4) Date: Oct. 28, 2008

(87) PCT Pub. No.: WO2006/018761
PCT Pub. Date: Feb. 23, 2006

(65) Prior Publication Data
US 2011/0103551 A1    May 5, 2011

Related U.S. Application Data

(60) Provisional application No. 60/601,288, filed on Aug. 13, 2004.

(51) Int. Cl.
*A61N 5/10* (2006.01)
(52) U.S. Cl. .......................................... 378/65; 382/131
(58) Field of Classification Search .................... 378/65; 382/128, 131, 132
See application file for complete search history.

(56) References Cited

U.S. PATENT DOCUMENTS

| | | | |
|---|---|---|---|
| 5,531,520 A | | 7/1996 | Grimson et al. |
| 5,633,951 A | * | 5/1997 | Moshfeghi .................... 382/154 |
| 5,859,891 A | * | 1/1999 | Hibbard .......................... 378/62 |
| 5,901,199 A | * | 5/1999 | Murphy et al. .................. 378/65 |
| 6,219,403 B1 | * | 4/2001 | Nishihara ........................ 378/65 |
| 6,226,418 B1 | * | 5/2001 | Miller et al. .................. 382/294 |
| 6,307,914 B1 | * | 10/2001 | Kunieda et al. ................. 378/65 |
| 6,385,286 B1 | | 5/2002 | Fitchard et al. |
| 6,735,277 B2 | | 5/2004 | McNutt et al. |
| 6,842,502 B2 | * | 1/2005 | Jaffray et al. ................... 378/65 |
| 6,888,919 B2 | * | 5/2005 | Graf ............................... 378/65 |
| 7,221,733 B1 | * | 5/2007 | Takai et al. ..................... 378/65 |
| 7,260,426 B2 | * | 8/2007 | Schweikard et al. .......... 600/407 |
| 7,280,710 B1 | * | 10/2007 | Castro-Pareja et al. ....... 382/303 |
| 7,302,286 B2 | * | 11/2007 | Camus et al. .................. 600/407 |
| 7,440,628 B2 | * | 10/2008 | Chefd'hotel .................. 382/236 |
| 7,536,041 B2 | * | 5/2009 | Pekar et al. .................... 382/128 |
| 7,596,207 B2 | * | 9/2009 | Kaus et al. ...................... 378/65 |
| 7,646,936 B2 | * | 1/2010 | Nord et al. .................... 382/294 |

(Continued)

OTHER PUBLICATIONS

Birkner, M., et al.; Adapting inverse planning to patient and organ geometrical variation: algorithm and implementation; Med. Phys.; 2003; 30(10)2822-2831.

(Continued)

*Primary Examiner* — Allen C. Ho

(57) ABSTRACT

In a radiation therapy method, one or more planning images are acquired (102) of a subject. Features of at least malignant tissue are contoured in the one or more planning images to produce one or more initial feature contours. One or more treatment images of the subject are acquired (114). The one or more initial feature contours are updated (122) based on the one or more treatment images. Radiation treatment parameters are optimized (126) based upon the updated one or more feature contours. Radiation treatment of the subject is performed (130) using the optimized parameters.

15 Claims, 2 Drawing Sheets

U.S. PATENT DOCUMENTS

Figure 1:
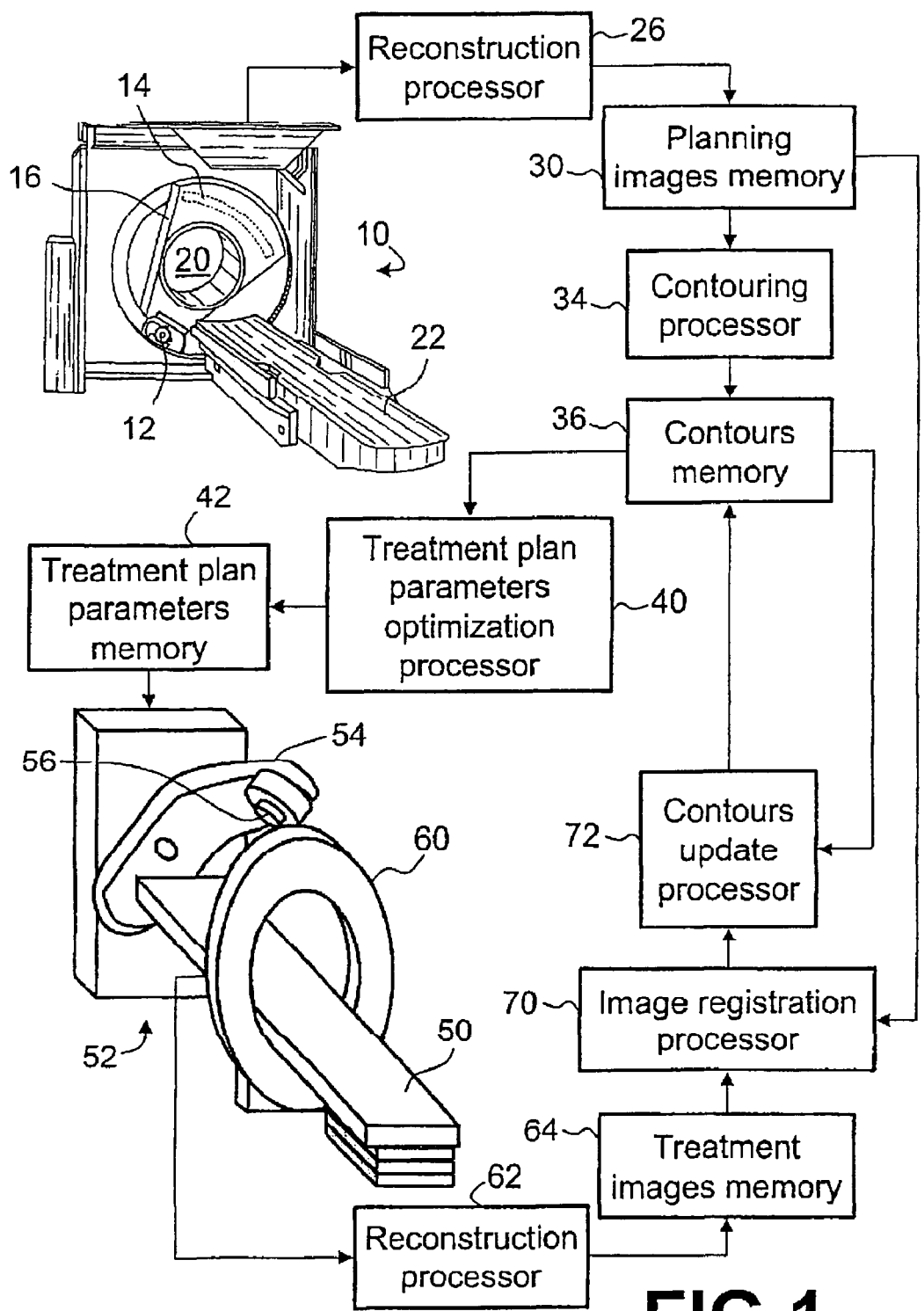

| | | | |
|---|---|---|---|
| 7,756,567 B2 * | 7/2010 | Kuduvalli et al. | 600/427 |
| 7,792,343 B2 * | 9/2010 | Pekar | 382/128 |
| 7,961,927 B2 * | 6/2011 | Gagnon et al. | 382/131 |
| 2002/0122530 A1 | 9/2002 | Erbel et al. | |
| 2002/0150207 A1 | 10/2002 | Kapatoes et al. | |
| 2003/0112922 A1 | 6/2003 | Burdette et al. | |

OTHER PUBLICATIONS

Brock, K. K., et al.; Inclusion of organ deformation in dose calculations; Med. Phys.; 2003; 30(3)290-295.

Hua, C., et al.; Development of a semi-automatic alignment tool for accelerated localization of the prostate; Int. J. Radiation Oncology Biol. Phys.; 2003; 55(3)811-824.

Jaffray, D.A., et al.; Flat-panel cone-beam computed tomography for image-guided radiation therapy; Int. J. Radiation Oncology Biol. Phys.; 2002; 53(5)1337-1349.

Killoran, J. H., et al.; A numerical simulation of organ motion and daily setup uncertainties: implications for radiation therapy; Int. J. Radiation Oncology Biol. Phys.; 1997; 37(1)213-221.

Lockman, D. M., et al.; Estimating the dose variation in a volume of interest with explicit consideration of patient geometric variation; Med. Phys.; 2000; 27(9)2100-2108.

Mackie, T. R., et al.; Image guidance for precise conformal radiotherapy; Int. J. Radiation Oncology Biol. Phys.; 2003; 56(1)89-105.

Maintz, J. B. A., et al.; A survey of medical image registration; Medical Image Analysis; 1998; 2(1)1-37.

Yan, D., et al.; Adaptive radiation therapy; Phys. Med. Biol.; 1997; vol. 42; pp. 123-132.

Yan, D., et al.; A model to accumulate fractionated dose in a deforming organ; Int. J. Radiation Oncology Biol. Phys.; 1999; 44(3)665-675.

Yan, D., et al.; Organ/patient geometric variation in external beam radiotherapy and its effects; Med. Phys.; 2001; 28 (4)593-602.

* cited by examiner

RADIOTHERAPEUTIC TREATMENT PLAN ADAPTATION

CROSS REFERENCE TO RELATED APPLICATIONS

This application claims the benefit of U.S. provisional application Ser. No. 60/601,288 filed Aug. 13, 2004, which is incorporated herein by reference.

The following relates to the radiation therapy arts. It finds particular application in intensity modulated radiation therapy employing high-energy xrays or gamma rays, and will be described with particular reference thereto. However, it also finds application in three-dimensional conformal radiation therapy and other types of radiation therapy generally, whether using x-rays, gamma rays, charged particle beams, or so forth, and whether using a tomographically revolved beam source or a plurality of fixed beam sources.

Radiation therapy is a powerful tool for combating cancers and certain other tissue malignancies. Ionizing radiation such as xrays, gamma rays, proton or neutron particles, or the like are applied to a cancerous tumor, a cancer-ridden organ, or other region containing malignant tissue. The ionizing radiation damages cellular DNA which can kill irradiated cells. Growing and rapidly multiplying cancer cells are typically more readily damaged by the radiation and less able to repair such damage than are healthy cells, providing built-in selectivity favoring elimination of cancerous tissue and survival of healthy tissue. To further reduce damage to healthy tissue, radiation therapy typically includes a series of treatments performed over several days or weeks. Performing radiation therapy as a series of treatments over an extended period of time facilitates healing of damaged non-cancerous tissue between treatments.

In conformal radiation therapy, the radiation beam is shaped to substantially conform to the shape of the profile of cancerous tumor or region from the direction of irradiation. One type of conformal radiation therapy is intensity modulated radiation therapy, in which the radiation beam, or a plurality of radiation beams, are intensity-modulated over the area of the beam using multileaved collimators or other beam-shaping elements. A plurality of beams at various angular positions around the subject can be employed, or a single beam can be tomographically revolved around the subject. In general, the integrated radiation dosage is highest in the region where the multiple beams intersect, or in the region near the center of tomographic rotation. A treatment plan including the appropriate selection of the beam locations, beam divergence angles, multileaved collimator settings, and so forth, controls the delivered radiation precisely to irradiate the cancerous region while limiting radiation exposure of sensitive nearby organs at risk.

A detailed CT planning image is generated prior to radiation treatment. The treatment plan is generated based on the planning image. One difficulty with radiation therapy is stability of the subject over time. During a series of radiation therapy sessions extending over an extended number of days or weeks, the organs at risk may change size, shape, orientation, position, or so forth. In some radiation therapy series, the cancerous tumor may shrink over time or otherwise change in positive response to the radiation therapy.

To account for the spatial variations, ultrasound, computed tomography imaging, or another positional monitor is used to realign the subject on the radiation therapy support table with the malignant tissue in the isocenter and orientation of the treatment plan. Aligning the patient as a whole cannot, however, address changes in the relative positions of the malignant tissue and the organs at risk. Nor can patient alignment address changes in the size, shape, or other characteristics of the tumor or of organs at risk.

The following contemplates improved apparatuses and methods that overcome the aforementioned limitations and others.

According to one aspect, a radiation therapy method is provided. A plurality of radiation treatment sessions are performed on a subject. Each session employs a pre-selected radiation treatment plan. At least some sessions include: (i) acquiring one or more treatment images of the subject; (ii) adjusting parameters of the radiation treatment plan based on the one or more treatment images to produce adjusted treatment plan parameters; and (iii) performing the radiation treatment plan using the adjusted treatment plan parameters.

According to another aspect, a radiation therapy method is provided. One or more planning images are acquired of a subject. Features of at least malignant tissue are contoured in the one or more planning images to produce one or more initial feature contours. One or more treatment images of the subject are acquired. The one or more initial feature contours are updated based on the one or more treatment images. Radiation treatment parameters are optimized based upon the updated one or more feature contours. Radiation treatment of the subject is performed using the optimized parameters.

According to another aspect, a radiation therapy system is disclosed for performing radiation therapy of a subject in accordance with a radiation treatment plan computed based on information representative of (i) malignant tissue to be irradiated and (ii) one or more organs at risk. The radiation therapy system includes a means for adjusting radiation treatment parameters of a previously selected radiation treatment plan based on treatment images to produce an adjusted treatment plan.

According to yet another aspect, a radiation therapy system is disclosed. A means is provided for acquiring one or more planning images of a subject. A means is provided for contouring features of at least malignant tissue in the one or more planning images to produce one or more initial feature contours. A means is provided for acquiring one or more treatment images of the subject. A means is provided for updating the one or more initial feature contours based on the one or more treatment images. A means is provided for optimizing radiation treatment parameters based upon the updated one or more feature contours. A means is provided for performing radiation treatment of the subject using the optimized parameters.

One advantage resides in increased accuracy of radiation delivery to malignant tissue and reduced collateral radiation damage to healthy tissue.

Another advantage resides in improved workflow efficiency during a series of radiation therapy sessions.

Yet another advantage resides in rapid and accurate adaptation of the treatment plan to changes in the position, orientation, size, shape, or radiosensitivity of the malignant tumor or organs at risk over the course of a series of radiation therapy sessions.

Numerous additional advantages and benefits will become apparent to those of ordinary skill in the art upon reading the following detailed description of the preferred embodiments.

The invention may take form in various components and arrangements of components, and in various process operations and arrangements of process operations. The drawings are only for the purpose of illustrating preferred embodiments and are not to be construed as limiting the invention.

FIG. 1 diagrammatically shows a radiation therapy system for performing a series of radiation therapy treatments.

Figure 2:
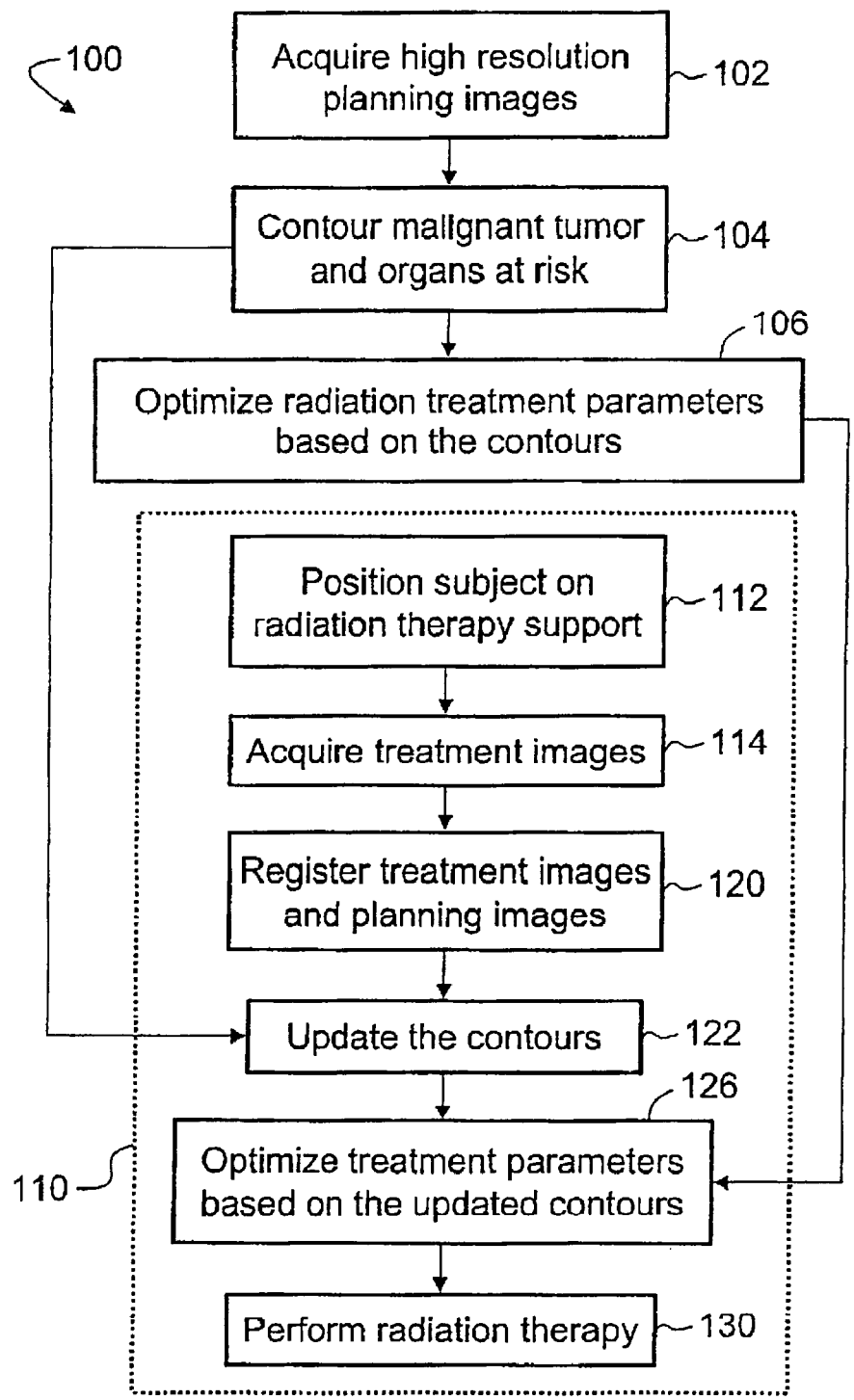

FIG. 2 flow charts a suitable radiation therapy workflow performed using the radiation therapy system of FIG. 1.

With reference to FIG. 1, a radiation therapy system includes a planning computed tomography imaging scanner 10. The illustrated scanner 10 includes a cone-beam xray source 12 and a two-dimensional x-ray detector array 14 mounted on a rotating gantry 16 on opposite sides of an imaging region 20. (Although these features are illustrated in FIG. 1 for expository purposes, it will be appreciated that typically the x-ray source 12, detector array 14, and rotating gantry 16 are enclosed in a stationary gantry housing). A radiation therapy subject, such as a cancer patient, is disposed on a patient support 22 and moved into the imaging region 20, and computed tomography projection data of the subject are acquired using the scanner 10. A reconstruction processor 26 employs filtered backprojection or another reconstruction algorithm to reconstruct the acquired projection data into one or more planning images of the radiation therapy subject which are stored in a planning images memory 30.

A contouring processor 34 is used to define and refine contours of the tumor and sub-tumor regions, which require a lesser or higher dose according to the functional information or other malignant tissue to be irradiated and, typically, contours of one or more organs at risk. For example, in the case of a patient with prostate cancer, the cancerous prostate is contoured, and nearby organs at risk of receiving excessive radiation exposure during the radiation therapy are also contoured. In the case of prostate radiation therapy, such organs at risk may include, for example, the rectum and the bladder. The contouring processor 34 can be a manual processor in which a radiation technician manually defines the contours using a graphical user interface or other tool, or the contouring processor 34 may be an automated processor that uses suitable pattern recognition algorithms to automatically identify and contour the tumor and organs at risk. Preferably, in the case of an automated processor the computed results are displayed for the radiation technician who can manually adjust or refine the contours. The resulting one or more contours are stored in a contours memory 36. Other anatomical data derived from the one or more planning images are also typically stored in the contours memory 36, such as radiation attenuation or tissue density information.

The anatomical information stored in the contours memory 36 is used by a radiation treatment plan parameters optimization processor 40 to determine optimized parameters for the radiation treatment plan. In intensity modulated radiation therapy, a plurality of radiation beams, or a single radiation beam tomographically revolved around the subject, are used to irradiate the tumor or other malignant tissue. The optimization processor 40 optimizes parameters such as: multileaved collimator settings that define the aperture shape; global beam intensity or weight; beam direction; wedge angle; fractionation schedule; and so forth using optimization criteria including at least: (i) producing substantial irradiation of the malignant tissue; and (ii) limiting irradiation of the organs at risk. The optimized treatment plan parameters are stored in a treatment plan parameters memory 42.

In developing the treatment plan including the optimized treatment plan parameters, high resolution three-dimensional images of the cancerous region are typically employed. The contouring of malignant tissue and organs at risk is temporally and computationally intensive. Three-dimensional planning images of high quality and high resolution are preferably used in performing the contouring.

Accordingly, the planning computed tomography scanner 10 is typically a high resolution multi-slice or cone beam scanner that images the subject typically some time in advance of the first radiation therapy session. For example, the subject may come into the radiation therapy clinic or another imaging facility for the planning imaging a few days or so in advance of the first radiation therapy session. This allows the radiation technician adequate time to perform accurate contouring in advance of initiation of radiation therapy.

At the first radiation therapy session, the subject is placed on a movable table or other subject support 50 associated with a radiation delivery system 52. Typically, the subject, or at least that portion of the subject which is to receive radiation therapy, is substantially immobilized on the subject support 50 using straps, clamps, cushions or other body restraints. In the illustrated embodiment, the radiation delivery system 52 is a tomographic system that includes a linear electron accelerator (i.e., linac) 54 producing an accelerated electron beam impinging upon a tungsten or other target to generate a beam of x-rays or gamma rays for irradiating the subject. A multileaved collimator 56 shapes or intensity modulates the x-ray or gamma ray beam. The radiation source is tomographically revolved about the subject during treatment to irradiate the subject over a range of angular views up to 360°. Instead of the illustrated tomographic radiation delivery system 52, other radiation delivery systems can be used, such as a multiple beam system in which a plurality of radiation sources are angularly spaced at fixed or adjustable angular positions around the subject gantry and produce multiple radiation beams that simultaneously or alternately irradiate the subject. For example, nine radiation sources can be arranged at 40° intervals around the subject. Each radiation source has a separate multileaved collimator to provide nine separately intensity-modulated radiation beams.

Prior to administering the radiation therapy, a second imaging system 60 images the subject. The subject support 50 preferably serves as a common subject support for both the radiation delivery system 52 and the second imaging system 60, and can linearly move the radiation therapy subject first into the imaging field of view of the second imaging system 60, and then subsequently into the radiation delivery system. In this way, the second imaging system 60 produces treatment images of the region to be irradiated in it's secured, immobilized position on the subject support 50.

The second imaging system 60 can be a second lower resolution computed tomography scanner (in which only the annular gantry housing is visible in the exterior view of FIG. 1). A reconstruction processor 62 reconstructs projection data acquired by the computed tomography scanner into one or more treatment images that are stored in a treatment images memory 64. Rather than a computed tomography scanner, other imaging modalities can serve as the second imaging system 60, such as an ultrasound imaging system, a fluoroscopy imaging system, a magnetic resonance imaging (MRI) scanner, a single photon emission computed tomography (SPECT) scanner, a positron emission tomography (PET) scanner, or the like. Moreover, in some embodiments a megavolt imaging scanner employs the radiation delivery system 52 as a megavolt radiation source for tomographic imaging.

An images registration processor 70 registers the one or more treatment images acquired by the second imaging system 60 with the one or more planning images previously acquired by the planning scanner 10. Substantially any type of image registration algorithm can be employed. In some embodiments, a voxel-based registration method employing an elastic function is used. Such registration methods advantageously operate in image space and are substantially independent of user inputs. Voxel-based registration methods which employ an elastic function deform one image or set of images to register with another image or set of images. Preferably, the planning images are deformed to register with the treatment images, but deforming the treatment images to register with the planning images is also contemplated.

Once the images are registered, a contours update processor 72 deforms or otherwise updates the contours representing the malignant tissue and the one or more organs at risk in accordance with the deformation required to register the images. The updated contours are stored in the contours memory 36 and are inputted to the treatment plan parameters optimization processor 40 which updates the treatment plan parameters based on the updated contours, and stores the updated parameters in the treatment plan parameters memory 42 for used in the upcoming radiation therapy session.

The treatment images and contour deformation computed therefrom account for changes in position, orientation, size, shape, and radiosensitivity of the tissue or organ. For example, over the course of several radiation therapy sessions for treating prostate cancer, the rectum, bladder, and other anatomical features can change in position, orientation, size, and shape due to different levels of fluid in the bladder, changes in the contents of the rectum, reduction in the size of cancerous tumors due to successful radiation therapy, or so forth.

With continuing reference to FIG. 1 and with further reference to FIG. 2, a suitable radiation therapy workflow 100 is described. In a process operation 102, high resolution planning images are acquired using the computed tomography scanner 10. The contouring processor 34 in a process operation 104 manually, semi-automatically, or automatically determines initial contours for the cancerous tumor, cancer-ridden organ, or other malignant tissue, and typically also determines contours for one or more radiation sensitive organs at risk, bone or other high density structures in the region, and the like.

Preferably, initial parameter values for the radiation treatment plan are determined in a parameters optimization process 106. The optimization is based on the initial anatomical and/or functional contours and other anatomical information derived from the planning images, such as radiation attenuation or tissue density information for the various tissues and organs in the vicinity of the cancerous tumor or organ. As a quantitative example, if there are nine discrete angular beam positions arranged at 40° intervals around the subject (achievable either by using nine fixed radiation sources or by using the illustrated single beam radiation source 52 with the beam tomographically moved through the nine positions) and each beam position has a 10×10 cm$^2$ beam area selectively divided into 0.5×0.5 cm$^2$ beamlets by a multileaved collimator, then there are 9×400=3600 beamlets to be optimized. Each of the nine radiation beams can also have global parameters such as overall beam intensity or weight, beam direction, wedge angle, fractionation schedule, and so forth. One optimization technique suitable for optimizing this large number of parameters is disclosed in McNutt et al., U.S. Pat. No. 6,735,277 (WO 03/099380).

Typically, the radiation therapy planning process operations 102, 104, 106 are performed in advance of the first radiation treatment session. The radiation therapy may be conducted in a single session, or, more typically, is divided into a plurality of radiation treatment sessions extending over a period of days, weeks, or longer. A workflow 110 for each radiation therapy session proceeds as follows. In a process operation 112, the subject is positioned on the subject support 50 with at least the portion of the subject to be irradiated substantially immobilized. The support 50 linearly moves the immobilized region into the field of view of the second imaging system 60 (or the second imaging system is moved to the patient). In a process operation 114, one or more treatment images are acquired using the second imaging system 60 associated with the radiation delivery system 52. In a process operation 120, the treatment images and the planning images are registered by the image registration processor 70 using a registration technique that elastically deforms one set of images to register it with another set of images. Some suitable registration techniques are provided, for example, in Maintz et al., "A Survey of Medical Image Registration", Medical Image Analysis, vol. 2 pp. 1-57 (1998). A voxel-based registration technique operating in image space is generally preferred. Landmarks-based or segmentation-based registration techniques can also be used, but these may require substantial user input.

Once the treatment and planning images are registered, in a process operation 122 the contours are updated by the contours update processor 72. For example, if the local image region corresponding to the bladder was isotropically elastically dilated by 5% by the image registration (perhaps due to fluid buildup in the bladder) then the contour representing the bladder is suitably correspondingly isotropically dilated by 5%. Similarly, rigid, affine, projective, curved, or other image registration transformations employed locally or globally are mapped to corresponding transformations of the contours to produce updated contours in the process operation 122.

Based on the updated contours, the treatment plan parameters are optimized in a process operation 126 by the treatment plan parameters optimization processor 40. If the optional initial optimization process operation 106 was performed, then the optimization process operation 126 is effectively a re-optimization and can use the initial treatment plan parameters determined in the initial optimization process operation 106 as starting values. Similarly, for second and subsequent radiation treatment sessions, the parameter values used in the previous treatment session can be used as starting values. Typically, employing starting parameter values that are close to optimal (which is usually the case when the starting parameter values are taken from the initial optimization 106 or from a previous radiation treatment session) results in high efficiency and rapid convergence of the optimization process 126. The parameter values determined by the optimization process operation 126 are stored in the treatment plan parameters memory 42 and are used in a process operation 130 during which radiation therapy is performed by the radiation delivery system 52.

Depending upon the rate and magnitude of changes in the irradiated region, in some cases the updating process operations 114, 120, 122 may be omitted from some radiation treatment sessions. For example, these updating process operations can be performed every other radiation treatment session, or every third radiation treatment session, or so forth. Moreover, if the registration process 120 indicates substantial stability of the irradiated region since the last treatment session, then the optimization process 126 is optionally omitted for the upcoming radiation treatment session.

Treatment images acquired by the second imaging system 60 are not used to construct the contours. Rather, the treatment images are only used to adjust the size, shape, orientation, position, or other spatial aspect of the contour. Accordingly, the second imaging system 60 typically produces images at a lower resolution versus the planning computed tomography scanner 10. This enables the second imaging system 60 to be a low-cost, low resolution imager that rapidly acquires the one or more treatment images. Moreover, the second imaging system 60 can employ a non-radiation based imaging modality such as ultrasound or magnetic resonance, since the treatment images are not used to extract information on radiation attenuation or tissue density for calibrating the treatment plan. (If, however, the second imaging system 60 is a computed tomography scanner or other imager that does provide tissue density information, it can be included in the updating operation 122.) The treatment images are used to provide relatively coarse information pertaining to the size, orientation, position, and general shape of the malignant tissue and the organs at risk.

Moreover, the planning images can incorporate functional or biological aspects. For example, in addition to computed tomography images that provide tissue radiation absorption and physical anatomy information, the planning images can include functional or biological images acquired using suitable imaging modalities such as single photon emission computed tomography (SPECT), positron emission tomography (PET), magnetic resonance spectroscopy (MRS), or so forth. Functional planning images can differentiate certain types of malignant tissue from healthy tissue based on functional or biological differences such as radiosensitivity.

Thus, in some contemplated embodiments, the planning images include functional or biological planning images having functional or biological contrast. Functional or anatomical features are contoured in the contouring process operation 104 to produce contours used in the optimization process 106. The treatment images correspondingly also include functional or biological images that are acquired in the process operation 114 using a suitable imaging modality providing the requisite functional or biological contrast. Theses functional or biological treatment images are registered in the registration process 120, and are used to update the corresponding contours in update process 122 to produce updated contours that are used in the updating optimization 126. These updates compensate for non-anatomical changes that impact the radiation treatment plan, such as changes in the radiosensitivity pattern of the malignant tumor, which may for example occur in response to local changes in oxygen partial pressure initiated by the irradiation (reoxygenation).

The functional or biological treatment images are not used for initial contouring and planning, but rather are used for corrective adjustment of the treatment plan. Hence, the functional or biological treatment images can be coarser images than the original planning images. Accordingly, the imaging system used to acquire the functional or biological treatment images is optionally a lower resolution system than the imaging system that acquired the functional or biological planning images. Indeed, the treatment imaging system can optionally employ a different imaging modality or combination of imaging modalities than the planning imaging system, so long as both provide the same type of functional or biological image contrast.

In some embodiments, multiple imaging modalities are employed to acquire the planning images. As one example, the planning imaging system includes a transmission computed tomography scanner used to acquire anatomical information and tissue radiation absorption characteristics, and a functional imaging modality used to acquire functional images such as radiosensitivity information. Features in the planning images are contoured, including anatomical features contoured using the transmission computed tomography images, and biological or functional features contoured using images acquired by the functional imaging modality. The treatment imaging system also includes a transmission computed tomography scanner and a functional imaging modality. The transmission computed tomography scanner produces treatment images from which the anatomical feature contours are updated, while the functional imaging modality produces treatment images from which the biological or functional feature contours are updated.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A radiation therapy method comprising:
performing a plurality of radiation treatment sessions on a subject, each radiation treatment session employing a parameterized radiation treatment plan having parameters with initial values of the parameters of the radiation treatment plan generated based on one or more planning images of the subject acquired prior to performing the plurality of radiation treatment sessions, at least some radiation treatment sessions including:
acquiring one or more treatment images of the subject prior to performing the radiation treatment plan,
registering the one or more treatment images with the one or more planning images using a voxel-based elastic function,
adjusting the initial values of the parameters of the radiation treatment plan prior to performing the radiation treatment plan based on elastic deformation indicated by the voxel-based elastic function to produce adjusted radiation treatment plan parameter values,
subsequent to the adjusting, storing the adjusted radiation treatment plan parameter values in a treatment plan parameters memory, and
subsequent to the acquiring, registering, adjusting, and storing, performing the radiation treatment plan using the adjusted radiation treatment plan parameter values stored in the treatment plan parameters memory.

2. The radiation therapy method as set forth in claim 1, wherein the initial values of the parameters of the radiation treatment plan were optimized from malignant tissue and organ at risk contours defined in the one or more planning images and wherein adjusting the initial values of the parameters of the treatment plan includes:
adjusting the malignant tissue and at risk organ contours in conformity with the elastic deformation indicated by the voxel-based elastic function; and
re-optimizing the values of the parameters of the treatment plan using the adjusted contours and using the initial values of the parameters of the treatment plan as starting values to generate the adjusted radiation treatment plan parameter values.

3. The radiation therapy method as set forth in claim 1, further comprising, prior to a first radiation treatment session of the plurality of radiation treatment sessions, determining the initial values of the parameters of the radiation treatment plan using a method comprising:
extracting at least one of anatomical, functional, and biological information from the one or more planning images including at least information on (i) malignant tissue to be irradiated and (ii) at least one organ at risk, and
optimizing the values of the parameters of the radiation treatment plan with respect to the extracted information to produce the initial values of the parameters of the treatment plan, the optimizing using criteria including at least (i) producing substantial irradiation of the malignant tissue and (ii) limiting irradiation of the at least one organ at risk.

4. The radiation therapy method as set forth in claim 3, wherein the one or more planning images were acquired using one or more planning imaging modalities, and the acquiring one or more treatment images employs one or more treatment imaging modalities at least one of which is different from the one or more planning imaging modalities.

5. The radiation therapy method as set forth in claim 4, wherein the one or more planning imaging modalities include a planning computed tomography imaging scanner operating at a planning imaging resolution and the one or more treatment imaging modalities include a planning computed tomography imaging scanner operating at a treatment imaging resolution lower than the planning imaging resolution.

6. The radiation therapy method as set forth in claim 4, wherein the one or more planning imaging modalities includes a computed tomography imaging scanner and the one or more treatment imaging modalities are selected from a group consisting of:
an ultrasound imaging scanner,
a magnetic resonance imaging scanner,
a computed tomography imaging scanner, and
a megavolt imaging scanner employing a radiation source used in the performing of the radiation treatment plan.

7. A radiation therapy method comprising:
acquiring one or more planning images of a subject;
contouring features of at least malignant tissue in the one or more planning images to produce an initial feature contour;
acquiring one or more treatment images of the subject;
updating the initial feature contour based on the one or more treatment images wherein the updating of the initial feature contour includes (i) registering the one or more treatment images with the one or more planning images using a voxel-based elastic function and (ii) adjusting the initial feature contour based on the registering wherein the adjusting includes adjusting a shape of the initial feature contour based on elastic deformation indicated by the voxel-based elastic function;
optimizing radiation treatment parameters based upon the updated feature contour; and
performing radiation treatment of the subject using the optimized radiation treatment parameters.

8. The radiation therapy method as set forth in claim 7, wherein the contoured features are selected from a group consisting of: (i) anatomical features, (ii) biological features, and (iii) functional features.

9. The radiation therapy method as set forth in claim 7, further including:
optimizing radiation treatment parameters based upon the one or more initial feature contours to produce starting parameter values,
wherein the optimizing based upon the updated one or more feature contours uses the starting parameter values as initial values for the optimizing.

10. The radiation therapy method as set forth in claim 7, further comprising:
repeating the performing of radiation treatment of the subject using the optimized parameters without repeating the optimizing.

11. A radiation therapy system comprising:
a first imaging system configured to acquire one or more planning images of a subject;
a contouring processor that contours features of at least malignant tissue in the one or more planning images to produce one or more initial feature contours;
a second imaging system configured to acquire one or more treatment images of the subject;
an image registration processor that registers the one or more treatment images with the one or more planning images using a voxel-based registration method employing an elastic function;
a contours update processor that deforms a shape of the one or more initial feature contours based on elastic deformation indicated by the elastic function of the image registration to generate an updated one or more feature contours;
a treatment plan parameters optimization processor that optimizes radiation treatment parameters based upon the updated one or more feature contours;
a treatment plan parameters memory, the treatment plan parameters optimization processor storing the optimized radiation treatment parameters in the treatment plan parameters memory; and
a radiation delivery system that performs radiation treatment of the subject using the optimized radiation treatment parameters stored in the treatment plan parameters memory.

12. The radiation therapy system as set forth in claim 11, wherein the second imaging system and the radiation delivery system include a common subject support.

13. The radiation therapy system as set forth in claim 11, wherein the first imaging system and the second imaging system each include at least one imaging modality selected from a group consisting of:
ultrasound imaging,
fluoroscopy imaging,
computed tomography imaging,
magnetic resonance imaging,
single photon emission computed tomography imaging,
positron emission tomography imaging, and
megavolt computed tomography imaging employing a radiation source used in performing radiation treatment of the subject.

14. An apparatus comprising:
a processor configured to update a radiation treatment plan generated using one or more initial feature contours delineating features including at least malignant tissue in one or more planning images acquired of a subject, the processor performing an update method including:
receiving one or more treatment images acquired of the subject,
updating the one or more initial feature contours based on the one or more treatment images wherein the updating of the one or more initial feature contours includes (i) registering the one or more treatment images with the one or more planning images using a voxel-based elastic function and (ii) adjusting the one or more initial feature contours based on the registering wherein the adjusting includes adjusting a shape of the one or more initial feature contours based on elastic deformation indicated by the voxel-based elastic function, and
optimizing radiation treatment parameters of the radiation treatment plan based upon the updated one or more feature contours.

15. The apparatus as set forth in claim 14, further comprising:
an imaging system configured to acquire the one or more treatment images of the subject.

* * * * *